United States Patent
Tai et al.

(10) Patent No.: US 11,234,615 B2
(45) Date of Patent: Feb. 1, 2022

(54) THREE-DIMENSIONAL FOLDING SELF-DRIVING FLEXIBLE RESPIRATION MONITORING SENSOR AND PREPARING METHOD THEREOF

(71) Applicant: University of Electronic Science and Technology of China, Sichuan (CN)

(72) Inventors: Huiling Tai, Sichuan (CN); Yadong Jiang, Sichuan (CN); Si Wang, Sichuan (CN); Bohao Liu, Sichuan (CN); Zhen Yuan, Sichuan (CN); Qi Huang, Sichuan (CN); Guangzhong Xie, Sichuan (CN)

(73) Assignee: University of Electronic Science and Technology of China, Sichuan (CN)

( * ) Notice: Subject to any disclaimer, the term of this patent is extended or adjusted under 35 U.S.C. 154(b) by 288 days.

(21) Appl. No.: 16/532,439

(22) Filed: Aug. 5, 2019

(65) Prior Publication Data
US 2019/0357808 A1    Nov. 28, 2019

(30) Foreign Application Priority Data

Jan. 28, 2019  (CN) .......................... 201910080965.9

(51) Int. Cl.
*A61B 5/087*    (2006.01)
(52) U.S. Cl.
CPC ...... *A61B 5/087* (2013.01); *A61B 2560/0214* (2013.01)

(58) Field of Classification Search
None
See application file for complete search history.

(56) References Cited

U.S. PATENT DOCUMENTS

| 2,999,495 A * | 9/1961 | Shipley | A61B 5/0935 600/541 |
| 3,512,521 A * | 5/1970 | Jones | A61B 5/097 600/541 |
| 5,984,872 A * | 11/1999 | Vriend | A61B 5/093 600/529 |
| 7,055,520 B2 * | 6/2006 | Swisa | A61B 5/087 128/200.24 |

FOREIGN PATENT DOCUMENTS

JP    5360897 B2 *  12/2013

\* cited by examiner

*Primary Examiner* — Michael R Bloch

(57) ABSTRACT

A three-dimensional folding self-driving flexible respiration monitoring sensor and the preparing method thereof is disclosed. In the present invention a first friction unit and a second friction unit are set on a bottom of the box, which comprise a substrate, a conductive electrode layer and a friction layer respectively; the second friction unit is fixed on the bottom of the box; a friction layer of the first friction unit faces a friction layer of the second friction unit; a back plate is set on a substrate of the first friction unit; a balloon is between the box and the back plate; an inlet tube connects the balloon and the box, which is on a side wall of the box; the conductive electrode layer of the first friction layer and the second friction layer are connected to the electrometer respectively. Micro-energy of the respiration is adopted to monitor the breathing.

8 Claims, 4 Drawing Sheets

THREE-DIMENSIONAL FOLDING SELF-DRIVING FLEXIBLE RESPIRATION MONITORING SENSOR AND PREPARING METHOD THEREOF

CROSS REFERENCE OF RELATED APPLICATION

The present application claims priority under 35 U.S.C. 119(a-d) to CN 201910080965.9, filed Jan. 28, 2019.

BACKGROUND OF THE PRESENT INVENTION

Field of Invention

The present invention relates to a power collection technique, MEMS (Microelectromechanical system) and breathing monitor field, and more particularly to a three-dimensional folding self-driving flexible respiration monitoring sensor and preparing method thereof.

Description of Related Arts

Breathing behavior is an important indicator for health. Compared with conventional blood test, colorimetry and etc. the respiratory exam is in real-time, sustainable, nondestructive and comfortable. Over the past decades, with the depletion of the fossil energy, an energy-friendly, low carbon, sufficient and attainable energy is in pressing demand. With the wide spread of the electronic products, the number of consumed batteries increases dramatically. The recycling of the toxic chemicals in the battery causes inevitable pollution and the frequent replacement of the batteries reduces the service years of the instruments. A self-powered respiration monitor is required to solve the problems of the conventional respiration monitors.

In 2012, the invention of TENG (triboelectric nanogenerator) provide a possibility to take advantage of the micro-energy, which is proved to be a high efficient instrument. The TENG is able to collect the micro-energy in various forms through a coupling of the triboelectrification and electrostatic induction. The TENG is able to transfer energy as wind, human motion and ocean power into electrical signals. The breathing is a kind of micro-energy, which is able to drive a TENG to complete a self-powered respiration monitor and to realize a self-initiated and self-powered respiration monitoring sensor. The self-powered respiration monitoring sensor breaks the limits of the conventional flexible sensor and finds a new way for a flexible wearable, non-destructive and multi parameters and is able to be widely applied.

SUMMARY OF THE PRESENT INVENTION

An object of the present invention is to provide a three-dimensional folding self-driving flexible respiration monitoring sensor and preparing method thereof to solve the problems of the conventional techniques. The present monitoring sensor is able to take full advantage of the micro-power of the respiration to realize a self-powered monitoring of the respiration. The present monitoring sensor has the following advantages which are easily driven by the breathing flow, easily prepared, low cost and suitable for mass production.

The technical solution of the present invention is as follow.

The three-dimensional folding self-driving flexible respiration monitoring sensor, comprising: a box, a first friction unit and a second friction unit in a wave form on a bottom of the box; wherein the first friction unit and the second friction unit comprise a substrate, a conductive electrode layer and a friction layer respectively; the second friction unit is fixed on the bottom of the box; a friction layer of the first friction unit faces a friction layer of the second friction unit; a back plate is set on a substrate of the first friction unit; a balloon is between the box and the back plate; an inlet tube passes and connects the balloon and the box; an outlet tube is on a side wall of the box; the balloon drives the first friction unit to touch and detach from the second friction unit through the back plate continuously under a force of respiration; the conductive electrode layer of the first friction unit and the second friction unit are connected to a electrometer though wires.

Specifically, a distance is between the first friction unit and the second friction unit. The first friction unit and the second friction unit touch each other while the balloon swells to the maximum extend to achieve the optimal output signal. The first friction unit is pushed toward the second friction unit while expelling the air. The first friction unit is pulled back while in-taking the air. The first friction unit and the second friction unit touch and detach from each other to induce charges on the conductive electrode layers of the first friction unit and the second friction unit to generate alternating output. The different expanding of the balloon changes the distance between the first friction unit and the second friction unit under different breathing flow, which changes output of the electrical signals and realizes the monitoring of the respiration. The breathing flow in the test is calibrated with a micro flow sensor.

Furthermore, the conductive electrode layer is a thin plate; the conductive electrode layer is produced with an aluminum, a nickel, a copper, a silver or a gold.

Furthermore, a thickness of the conductive electrode layer is 100-200 nm to ensure smooth conduction and induction.

Furthermore, the substrate is an organic thin-film which is produced with a PET (Polyethylene terephthalate) or a PI (Polyimide).

Furthermore, the friction layer of the first friction unit is with positive charge; the friction layer of the first friction unit is produced with a nylon, a PU(Polyurethane) foam, a paper or metals. Nylon is an optimal choice.

Furthermore, the friction layer of the second friction unit is with negative charge; the friction layer of the second friction unit is produced with a PTFE (Polytetrafluoroethylene), a PDMS (Polydimethylsiloxane), a PVC (Polyvinyl Chloride) or the PI. PTFE is an optimal choice.

Furthermore, a thickness of the friction layer of the first friction unit is 100-250 μm; a thickness of the friction layer of the second friction unit is 100-250 μm.

Furthermore, a test blowing nozzle and a flow limiting valve are set on the inlet tube.

A method for preparing the three-dimensional folding self-driving flexible respiration monitoring sensor comprises the following steps:

(1) cleaning two pieces of flexible organic films with DI (deionized) water before drying the two pieces of flexible organic films as materials to produce the substrates;

(2) depositing a layer of conductive electrode material on the two pieces of flexible organic films to achieve two similar conductive electrodes;

(3) applying a layer of material with positive charge on a surface of the conductive electrode; modifying the surface of the conductive electrode by a laser or an embossing template to roughen the surface of the conductive electrode and achieve a first friction unit; bending and shaping the first friction unit at a specific angle; fixing the back plate on a surface of the substrate of the first friction unit;

(4) applying a layer of material with negative charge on a surface of the conductive electrode; nano micrometer modifying the surface of the conductive electrode by a laser or an embossing template to achieve a second friction unit; bending and shaping the second friction unit at the same specific angle with the first friction unit;

(5) cutting and assembling an insulating encapsulating material into a box by a laser cutting machine; wherein the insulating encapsulating material is able to be choose from PMMA (Poly(methyl methacrylate)), insulating paper plate, rubber plate, plastic plate and ceramic plate, which is convenient for following assembly.

(6) fixing the second friction unit prepared in the step (4) on one side of the box; leading out a wire from the conductive electrode layer of the second friction unit; placing the movable back plate at the bottom of the box; fixing the balloon in the middle of the back plate; connecting an inlet end of the balloon to the inlet tube; fixing the inlet tube on a side with the test blowing nozzle; leading out a wire from the conductive electrode layer of the first friction unit;

(7) connecting a flow limiting valve on the inlet tube on the box; assembling a test blowing nozzle on the flowing limiting valve for easily connecting respiration flow; pulling and pushing the first friction unit to touch and detach from the second friction unit by an expanding and contracting of the balloon while respiration to generate an alternating electrical signal output; and (8) collecting data with an electrometer; calculating a number of an output of waves within a time unit, which is a frequency of the respiration; measuring a flow of the respiration by observing an output of amplitudes.

Furthermore, referring to an optimal embodiment, the model of the electrometer is Keithley 6514.

Comparing to the conventional techniques, the present invention has the following benefits. The respiration monitoring sensor of the present invention is self-powered by breathing flow to realize a self-initiated monitor of the respiration. The present invention does not require external power supply. The structure of the present invention is simple. The output signals are stable. The present invention is convenient for carrying and assembly. The present invention is not demanding for materials and low cost for production. The present invention is able to be widely applied in respiration monitor field.

Element number: 1—box, 2—first friction unit, 3—second friction unit, 4—back plate, 5—balloon, 6—inlet tube, 7—flow limiting valve, 8—test blowing nozzle, 9—electrometer, 10—data collective computer, 11—wire, 13—outlet tube, 21,31—substrate, 22,32—conductive electrode layer, 23,33—friction layer.

DETAILED DESCRIPTION OF THE PREFERRED EMBODIMENT

Referring to FIG. 1 to FIG. 9 of the drawings according to a preferred embodiments of the present invention is illustrated. The embodiments are not limitations of the present invention. Any modifications or alterations of the present invention by skilled technician in the field are within the protection group of the present invention.

Embodiment 1

Figure 8:
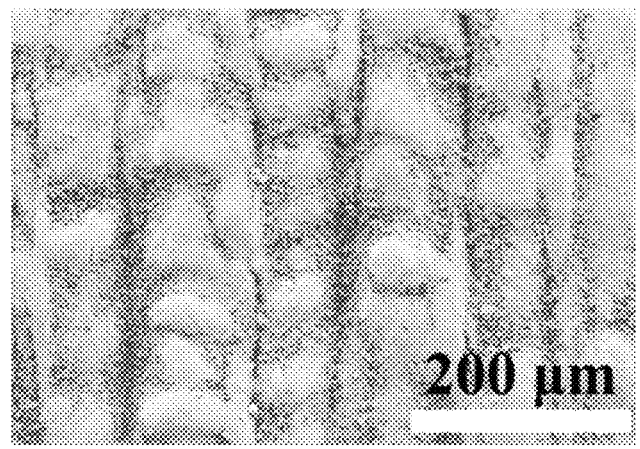
FIG. 8 is PTFE film surface morphologies after modified by femtosecond laser.

The preparing method of the three-dimensional folding self-driving flexible respiration monitoring sensor comprises the following steps:

(1) cleaning two pieces of flexible organic films with DI (deionized) water before drying the two pieces of flexible organic films as materials to produce the substrates 21 and 31; wherein the two pieces of flexible organic films is 12 cm in length, 3 cm in width and 0.1-0.25 mm in thickness;

(2) depositing a layer of conductive electrode material on the two pieces of flexible organic films to achieve two similar conductive electrodes;

(3) applying a layer of nylon with positive charge on a surface of the conductive electrode; modifying the surface of the conductive electrode by a laser to roughen the surface of the conductive electrode and achieve a first friction unit 2; bending and shaping the first friction unit 2 at a specific angle; fixing the back plate 4 on a surface of the substrate 21 of the first friction unit;

(4) applying a layer of PTFE (Polytetrafluoroethylene) with negative charge on a surface of the conductive electrode; nano micrometer modifying the surface of the conductive electrode by an embossing template to achieve a second friction unit 3; bending and shaping the second friction unit 3 at the same specific angle with the first friction unit 2; modifying a surface of the PTFE film with a femtosecond laser generated by a Ti: sapphire laser (Spectra-Physics, America) to increase the friction charge on the surface; wherein the laser pulse length, center wavelength, frequency and scanning speed are set to 100 fs, 80 nm, 1 kHz and 0.5 mm/s respectively; the surface morphologies of the PTFE film after modified is shown in the FIG. 8;

(5) finding a PMMA (Polymethyl methacrylate) plate with a thickness of 3 mm; cutting and assembling the PMMA plate into a box 1 (12 cm long, 10 cm wide and 10 cm high) by a laser cutting machine;

(6) fixing the second friction unit 3 prepared in the step (4) on one side of the box 1; leading out a wire 11 from the conductive electrode layer of the second friction unit 3; fixing the balloon 5 on the back plate 4 of the first friction unit 2 prepared in the step (3); connecting an inlet end of the balloon 5 to the inlet tube 6 with a diameter of 6 mm; fixing the inlet tube 6 on a side with the test blowing nozzle; leading out a wire 11 from the conductive electrode layer of the first friction unit;

(7) connecting a flow limiting valve 7 on the inlet tube 6 on the box 1; assembling a test blowing nozzle 8 on the flowing limiting valve 7 for easily connecting respiration flow; pulling and pushing the first friction unit 2 to touch and detach from the second friction unit 3 by an expanding and contracting of the balloon 5 while respiration to generate an alternating electrical signal output; and (8) collecting data with an electrometer 9 (Keithley 6514); calibrating a breathing flow in the test with a micro flow sensor (MF5700); calculating a number of an output of waves within a time unit, which is a frequency of the respiration; measuring a flow of the respiration by observing an output of amplitudes; collecting the data with the data collection computer 10.

Figure 1:
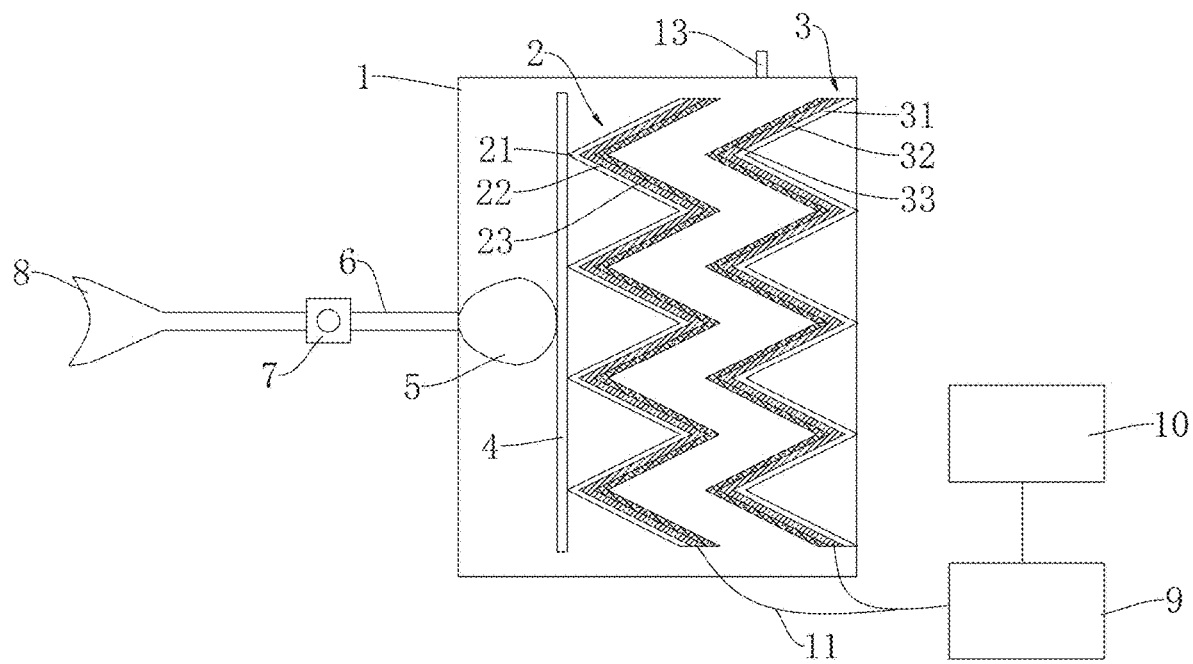
FIG. 1 is a perspective view of three-dimensional folding self-driving flexible respiration monitoring sensor.
Figure 2:
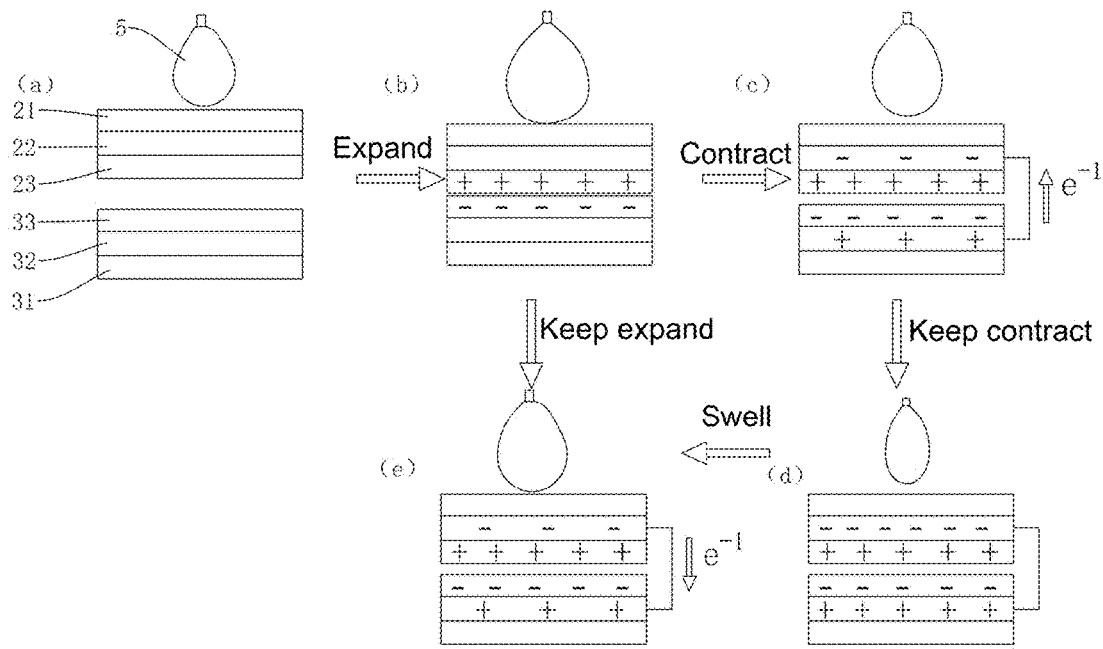
FIG. 2 is an indication of the working mechanism of the three-dimensional folding self-driving flexible respiration monitoring sensor.
Figure 3:
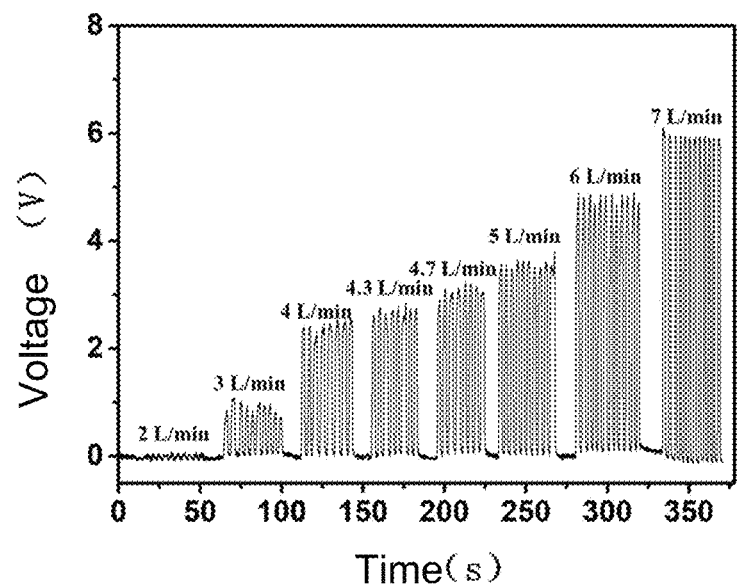
FIG. 3 is respond of the three-dimensional folding self-driving flexible respiration monitoring sensor.
Figure 4:
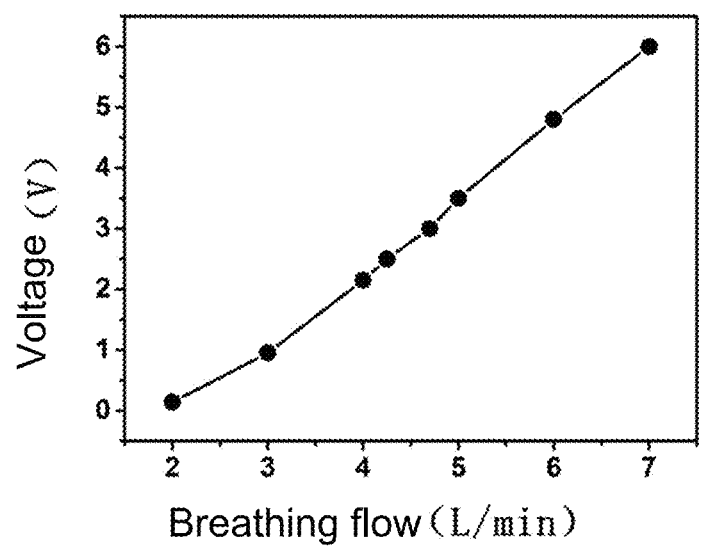
FIG. 4 is a curve to indicate changes of the output voltage of three-dimensional folding self-driving flexible respiration monitoring sensor with the change of breathing flow.
Figure 5:
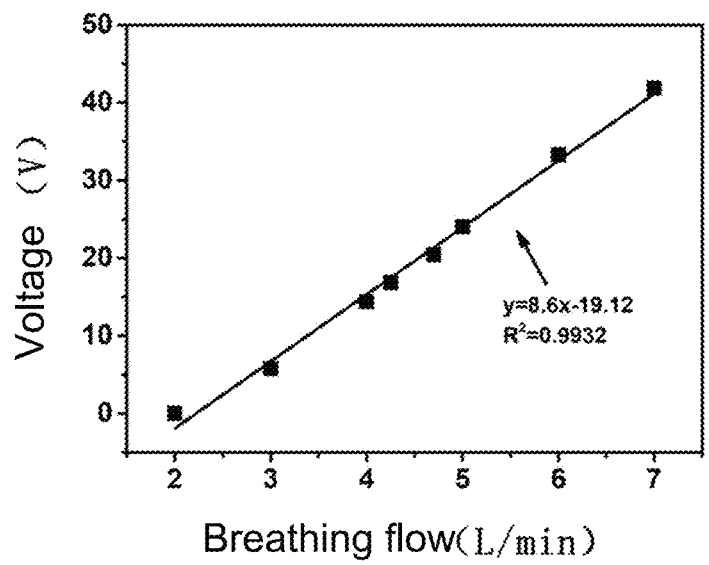
FIG. 5 is a linear regression graph of responses to different breathing flow of the three-dimensional folding self-driving flexible respiration monitoring sensor.
Figure 6:
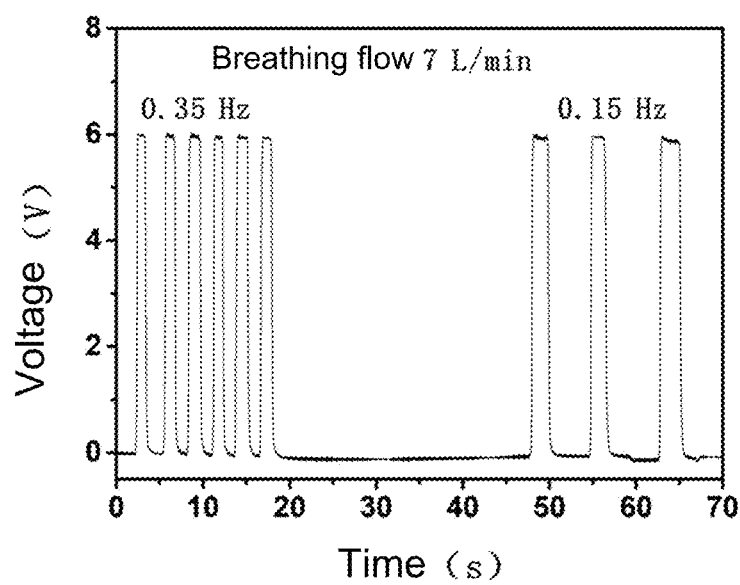
FIG. 6 is an indication of different frequencies effects on the three-dimensional folding self-driving flexible respiration monitoring sensor under constant breathing.
Figure 7:
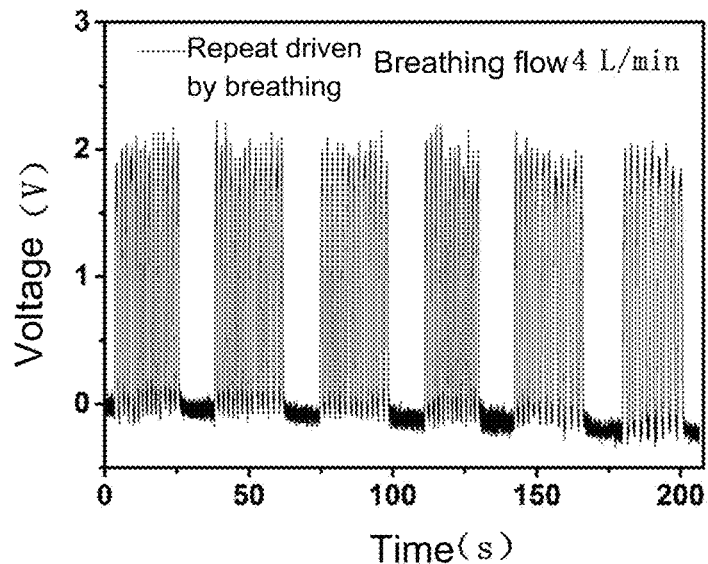
FIG. 7 is a repeatability test graph of the three-dimensional folding self-driving flexible respiration monitoring sensor under constant breathing.

Referring to the FIG. 2, the working mechanism is as follow: the air flows into the balloon 5 while breathing; the expanding of the balloon 5 push the back plate 4; the back plate 4 push the first friction unit 2 to get close to the second friction unit 3; the electronics are attracted from the material with weak electronegativity to material with strong electronegativity until the interfaces are laden with equal but opposite charges which is friction charges (FIG. 2(b)); the balloon 5 slowly contracts while people in-taking airs and no air flows into the balloon 5; the two surfaces of the friction layers detaches and a potential difference is emerged; the conductive electrode layer generates induced charge to screen the electrostatic potential (FIG. 2(d)); the density of the induced charge on the conductive electrode layer reaches the peak (FIG. 2 (d)) when two surfaces of the friction layer are farthest to each other and the density of the induced charge on the conductive electrode layer is highest (2(d)); Once the two surfaces of the friction layers contact again the electronics flows reversely (2(e)); the first friction unit 2 and the second friction unit 3 forms a nanogenerator and output alternative current pulses by touching and detaching of the friction layers.

The back plate 4 assists the collection of the pressing force caused by the expanding of balloon 5 and the movement of first friction unit 2. The output signals are decided by every respiration cycle. The breathing frequency of different people is able to be monitored by counting the output pulses within a time unit. The magnitude of the output is relevant to the breathing flow, which enables a real-time and in time help for critically ill patient. The results are illustrated in FIG. 3, FIG. 4, FIG. 5, FIG. 6 and FIG. 7.

Embodiment 2

The structure of the three-dimensional folding self-driving flexible respiration monitoring sensor in the embodiment is similar with the embodiment 1. The embodiment 2 differs from embodiment 1 in the following aspects: the friction layer 33 of the second friction unit 2 adopts PDMS (Polydimethylsiloxane) film to improve the output signals of the friction nanogenerator; the surface of the PDMS film is modified by embossing template to arrange the surface of the film with aligned embosses. The steps are as follow:

(1) drawing pattern template by Auto CAD;
(2) cutting the PMMA plate according to the designed pattern by a laser cutting machine;
(3) bathing the PMMA plate in 80° C. of TMCS (Trimethylsilyl chloride) for one hour's of ydrophobic treatment;

(4) mixing and stirring evenly the PDMS solution and the hardener with a ratio of 10:1; vacuuming for 30 minutes to remove the bubbles in the solution;

(5) dropping the PDMS solution on the PMMA plate; settling the plate in normal room temperature for four hours before drying under 60° C. for 24 hours;

(6) stripping the PDMS film off from the PMMA plate to achieve a film with modified micro-structure.

Figure 9:
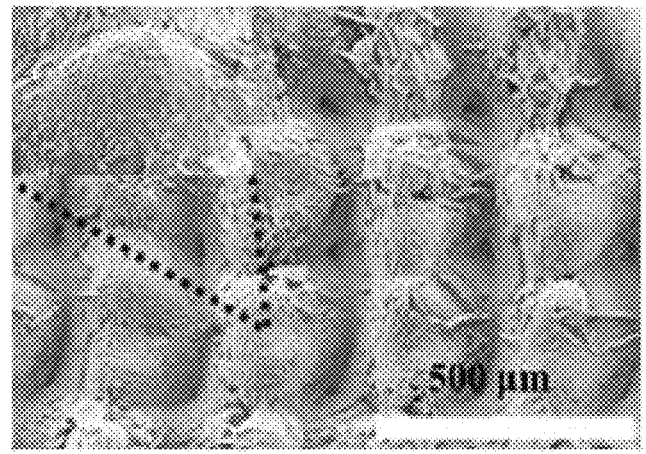
FIG. 9 is PDMS film surface morphologies after modified by an embossing template.

The surface of the modified PDMS film by embossing template is shown in FIG. 9.

The embodiments have been shown and described for the purposes of illustrating the functional and structural principles of the present invention and is subject to change without departure from such principles. The embodiments are not limitations of the present invention. Therefore, this invention includes all modifications encompassed within the spirit and scope of the following claims.

What is claimed is:

1. A three-dimensional folding self-driving flexible respiration monitoring sensor, comprising:
a box;
a first friction unit and a second friction unit, each in a wave form, on a bottom of the box;
wherein each of the first friction unit and the second friction unit comprise a substrate, a conductive electrode layer and a friction layer;
the second friction unit is fixed on the bottom of the box;
the friction layer of the first friction unit faces the friction layer of the second friction unit;
a back plate is set on the substrate of the first friction unit;
a balloon is between the box and the back plate;
an inlet tube passes and connects the balloon and the box; and
an outlet tube is on a side wall of the box;
wherein the balloon drives the first friction unit to touch and detach from the second friction unit through the back plate continually under a force of respiration.

2. The three-dimensional folding self-driving flexible respiration monitoring sensor, as recited in claim 1, wherein for each of the first friction unit and the second friction unit the conductive electrode layer is a thin plate; and for each of the first friction unit and the second friction unit the conductive electrode layer is produced with an aluminum, a nickel, a copper, a silver, or a gold.

3. The three-dimensional folding self-driving flexible respiration monitoring sensor, as recited in claim 1, wherein for each of the first friction unit and the second friction unit a thickness of the conductive electrode layer is 100-200 nm.

4. The three-dimensional folding self-driving flexible respiration monitoring sensor, as recited in claim 1, wherein for each of the first friction unit and the second friction unit the substrate is an organic thin-film which is produced with a PET (Polyethylene terephthalate) or a PI (Polyimide).

5. The three-dimensional folding self-driving flexible respiration monitoring sensor, as recited in claim 1, wherein the friction layer of the first friction unit is with positive charge; and the friction layer of the first friction unit is produced with a nylon, a PU (Polyurethane) foam, a paper or metals.

6. The three-dimensional folding self-driving flexible respiration monitoring sensor, as recited in claim 1, wherein the friction layer of the second friction unit is with negative charge; and the friction layer of the second friction unit is produced with a PTFE (Polytetrafluoroethylene), a PDMS (Polydimethylsiloxane), a PVC (Polyvinyl Chloride) or a PI.

7. The three-dimensional folding self-driving flexible respiration monitoring sensor, as recited in claim 1, wherein a thickness of the friction layer of the first friction unit is 100-250 μm; and a thickness of the friction layer of the second friction unit is 100-250 μm.

8. The three-dimensional folding self-driving flexible respiration monitoring sensor, as recited in claim 1, further comprising a test blowing nozzle and a flow limiting valve set on the inlet tube.

* * * * *